(12) United States Patent
Neculaes et al.

(10) Patent No.: US 8,778,682 B2
(45) Date of Patent: Jul. 15, 2014

(54) OPTICAL BASED DELIVERY OF EXOGENOUS MOLECULES TO CELLS

(75) Inventors: Vasile Bogdan Neculaes, Niskayuna, NY (US); Kenneth Roger Conway, Clifton Park, NY (US); Allen Lawrence Garner, Clifton Park, NY (US); Evelina Roxana Loghin, Rexford, NY (US); Siavash Yazdanfar, Niskayuna, NY (US); Dmitry Vladimirovich Dylov, Schenectady, NY (US); Brian Michael Davis, Albany, NY (US); Chulmin Joo, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 47 days.

(21) Appl. No.: 13/221,161

(22) Filed: Aug. 30, 2011

(65) Prior Publication Data
US 2013/0052738 A1 Feb. 28, 2013

(51) Int. Cl.
*C12N 15/87* (2006.01)
*C12N 13/00* (2006.01)

(52) U.S. Cl.
CPC ............ *C12N 13/00* (2013.01); *C12N 15/87* (2013.01)
USPC .................. 435/460; 435/173.4; 435/173.5; 435/455

(58) Field of Classification Search
None
See application file for complete search history.

(56) References Cited

U.S. PATENT DOCUMENTS

| | | | |
|---|---|---|---|
| 5,013,660 A | 5/1991 | Kasuya et al. | |
| 6,346,101 B1 | 2/2002 | Alfano et al. | |
| 6,670,129 B2 | 12/2003 | Webb et al. | |
| 7,709,047 B2 | 5/2010 | Emmert-Buck et al. | |
| 7,892,837 B2 | 2/2011 | Koenig et al. | |
| 2002/0076744 A1 | 6/2002 | Koller et al. | |
| 2005/0095578 A1 | 5/2005 | Koller et al. | |
| 2006/0141624 A1 | 6/2006 | Koenig et al. | |
| 2008/0057558 A1 | 3/2008 | Niwa et al. | |
| 2008/0176332 A1 | 7/2008 | Berns et al. | |
| 2009/0326614 A1 | 12/2009 | El-Sayed et al. | |
| 2010/0206731 A1 | 8/2010 | Lau et al. | |
| 2010/0209963 A1 | 8/2010 | Dave et al. | |
| 2011/0117648 A1 | 5/2011 | Chiou et al. | |

FOREIGN PATENT DOCUMENTS

GB 2262163 A 6/1993
WO 2009140701 A2 11/2009

OTHER PUBLICATIONS

Soman et al. J Biomed Nanotechnol Jun. 2011;7:334-41.*
Medarova et al. Nat Med 2007;13:372-7.*
Search Report and Written Opinion from corresponding PCT Application No. PCT/EP2012/066796 dated Nov. 9, 2012.
Tirlapur et al., "Targeted transfection by femtosecond laser", Nature: International Weekly Journal of Science, vol. 418, No. 6895, pp. 290-291. Jul. 18, 2002.
Zeira et al., "Femtosecond infrared laser—an efficient and safe in vivo gene delivery system for prolonged expression.", Molecular Therapy: The Journal of the American Society of Gene Therapy Aug. 2003 LNKD-Pubmed:12907157, vol. 8, No. 2, pp. 342-350, Aug. 2003.
Tsen et al., "Femtosecond laser treatment enhances DNA transfection efficiency in vivo", Journal of Biomedical Science 2009 LNKD-Pubmed: 19338665, vol. 16, pp. 1-7, 2009.
Bruneel et al., "Flexible Tool for Two-Photon Laser Nanoprocessing and Large Area Mapping with High Resolution", Optics and Lasers in Engineering, vol. 48, No. 12, pp. 1278-1284, Dec. 2010.
Straub et al., "Efficient Nanostructure Formation on Silicon Surfaces and in Indium Tin Oxide thin Films by Sub-15 fs Pulsed Near-Infrared Laser Light", Physics Procedia, vol. 12, No. 2, pp. 16-23, 2011.
Kate Rhodes et al.; "Cellular Laserfection", Methods in Cell Biology, vol. 82 0091-679X/07 $35.00: Copyright 2007, Elsevier Inc. All rights reserved; 25Pages.
Hester et al.; "Targeted transfection by femtosecond laser"; Stephens, D. J. & Pepperkok, R. Proc. Natl Acad. Sci. USA 98,4295-4298 (2001).290 Nature I vol. 418 I Jul. 18, 2002 I www.nature.com/nature; 2Pages.
Cheng Peng et al.; "Femtosecond near-infrared opto-injection of single living cells: pore size in dependence of laser intensity"; Optical Interactions with Tissue and Cells XVII, edited by Steven L. Jacques, William P. Roach, Proc. of SPIE vol. 6084, 608413, (2006) • 1605-7422/06/$15 • doi: 10.1117/12.644342; 8Pages.
Search Report and Written Opinion from corresponding PCT Application No. PCT/EP2012/066797 dated Nov. 8, 2012.

* cited by examiner

*Primary Examiner* — Janice Li
(74) *Attorney, Agent, or Firm* — Jenifer E. Haeckl

(57) ABSTRACT

A method of delivering exogenous molecules, comprising: providing a plurality of cells having a cell membrane; adding a plurality of exogenous molecules to the cells; exposing the cells to a defocused infrared (IR) light to permeabilize the cell membrane of the cells; and delivering the exogenous molecules to the cells through the permeablized cell membrane, wherein an intensity of the IR light at the optical focus is at least greater than or equal to an order of $10^4$ W/cm$^2$.

21 Claims, 7 Drawing Sheets

OPTICAL BASED DELIVERY OF EXOGENOUS MOLECULES TO CELLS

TECHNICAL FIELD

The invention relates generally to methods for delivering foreign materials to the living cells using optical means, and more specifically, the invention relates to methods for delivering exogenous molecules to the living cells using infrared (IR) light.

BACKGROUND OF THE INVENTION

The introduction of exogenous molecules into cells plays a significant role in recombinant technology, therapeutic applications, genetic analysis, cell tracking or cell trafficking. For example, delivery of genetic materials into cells is a key technique in recombinant DNA technology and has immense importance in genetic analysis. In transfection, the cells are administered with naked DNA, which are introduced into the cells to produce an RNA and/or protein.

A successful delivery of exogenous molecules into cells in an in vitro system can be achieved by various techniques to improve efficiency of the delivery technique without perturbing the structure or function of the cells. One or more techniques are known in the art to introduce exogenous molecules into the cells which include, but are not limited to, microinjection, liposome based cell fusion, electroporation, and ballistic methods. Moreover, pulse electric field and diagnostic ultrasound are presently used for permeabilization of cells. Among these techniques, electroporation has been used for various types of cell transfection, though it is largely disruptive and causes cellular death.

To increase the efficiency and to minimize the side effects of various methods, optical-based delivery was introduced. For example, laser based microinjection, optoinjection or optoporation are used for gene delivery. Use of lasers for cell transfection is an efficient method, and the hole formed by the laser beam is found to repair itself within a short time span. In optoporation, either permeability of the cell membrane is changed or pore formed at the site of the laser beam contact on the plasma membrane, and these techniques do not damage the cells extensively. In most of the optoporation techniques, the permeability of the cells is modified at the site at which the laser impacts the cell membrane. However, the methods of laser based microinjection, optoinjection or optoporation presently employ high numerical aperture, or expensive light sources (e.g., solid-state lasers) and the methods only allow for low throughput because they are generally focused on single cell transfection.

Therefore, optical based delivery techniques which are inexpensive and provide high throughput molecular delivery into cells with high transfection efficiency are desirable.

BRIEF DESCRIPTION OF THE INVENTION

One or more of the methods of invention overcome many of the disadvantages of the delivery methods known in the art. One or more of the examples of the methods of the invention are able to transfect exogenous molecules to the cells without affecting cell viability in an inexpensive way.

In one example, a method of delivering exogenous molecules comprises, providing a plurality of cells having a cell membrane; adding a plurality of exogenous molecules to the medium containing the cells; exposing the cells to an infrared (IR) light to permeabilize the cell membrane; and delivering the exogenous molecules to the cells through the permeabilized cell membrane, wherein an average power density of the IR light at the optical focus is greater than or equal to an order of $10^4$ W/cm$^2$, and a peak power density is greater than or equal to an order of $10^8$ W/cm$^2$.

In one example, a method of ablating cells comprises, providing a plurality of cells; and exposing the cells to a focused IR light, wherein an average power density of the IR light at the optical focus is at least greater than or equal to an order of $10^5$ W/cm$^2$.

BRIEF DESCRIPTION OF THE DRAWINGS

These and other features of embodiments of the invention will be more readily understood from the following detailed description of the various aspects of the invention taken in conjunction with the accompanying drawings that depict various embodiments of the invention, in which.

DETAILED DESCRIPTION OF THE INVENTION

Optical based delivery enables exogenous molecules to be introduced into the cells without compromising the viability of the cells, cellular expansion, death, and differentiation. The method comprises providing a plurality of cells, adding exogenous molecules to the cells, exposing the cells to an infrared (IR) light source and delivering the exogenous molecules to the exposed cells.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, "area of irradiation" refers to an area over which a defocused IR radiation is incident. The cells are typically present on that area of incident and consequently are being irradiated by the IR light. The cells are exposed to IR over the area of irradiation.

As used herein, "exogenous molecules" refers to the molecules which are not present or derived outside the cells. The exogenous molecules may be transferred to the cells from outside. The exogenous molecules may comprise genetic materials (such as DNA or RNA), proteins, peptides, or small molecules (such as dyes).

As used herein, "thermal gradient" refers to a rate of temperature change with distance. For example, a temperature difference across the cell membrane, from the direction of outside to the inside of the cell provides a thermal gradient. The thermal gradient may be generated based on light absorption of the water molecules present in the liquid media (comprising the cells) and lipid molecules of the cell membrane.

As used herein, "target sequence" refers to a sequence that code for an expression product. In some examples, the expression product may be able to elicit an immune response in an organism. The target sequence codes for a surface antigen of the bacterium, virus, fungus, parasitic organism, or non-parasitic organism from which it is derived.

Figure 6:
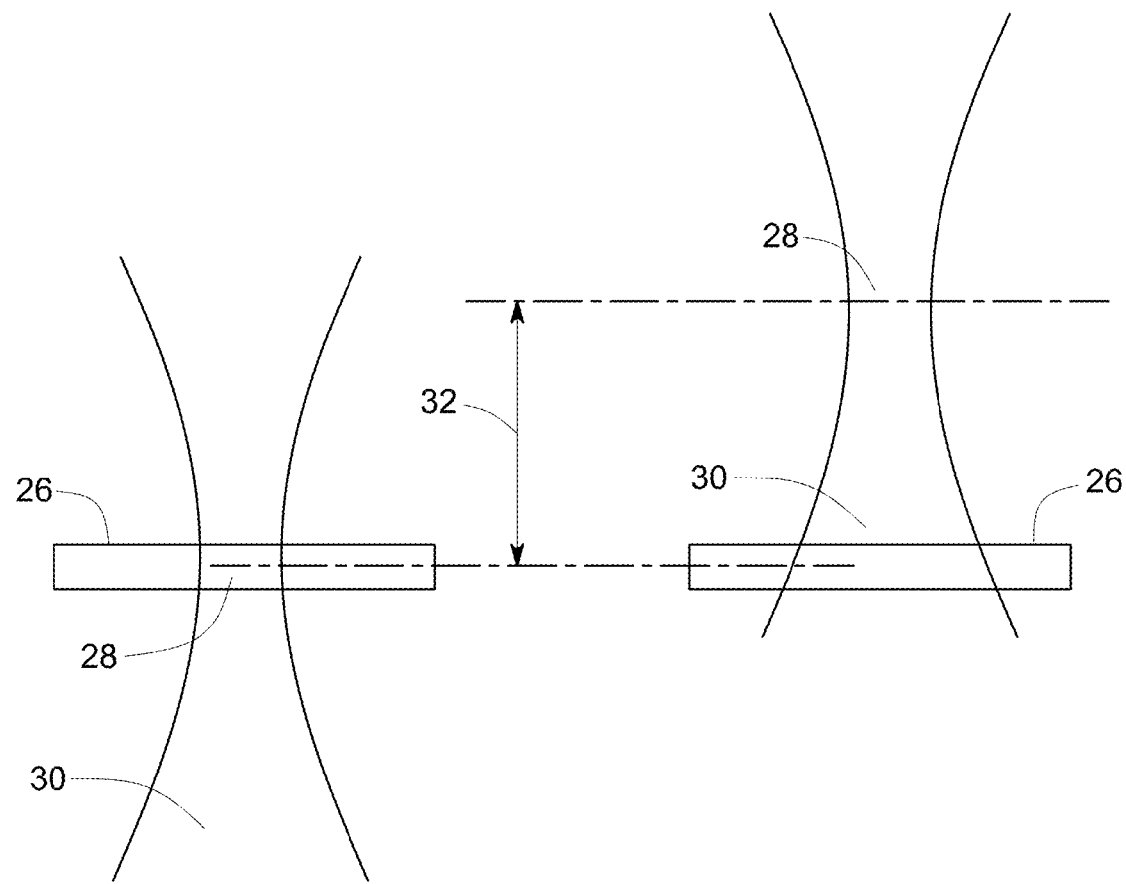
FIG. 6 is a schematic presentation illustrating vertical adjustment of laser focusing on cells according to an embodiment of the invention

As used herein, "vertical adjustment of the laser focusing" refers to an adjustment method that positions the optical focus along the optical axis where the laser intensity is modified by shifting one or more optical components (such as, lenses or mirrors) towards or away from a sample holder (e.g., FIG. 6). Vertical adjustment may be necessary to control the efficiency of delivery of exogenous molecules. such as transfection, or ablation control for a particular cell type. In some applications, this can be done with manually, automatic translation stages, variable focus lenses and wavefront modulators.

As used herein, "high throughput" refers to a method for delivery of exogenous molecules to multiple cells at a time. The number of cells for high throughput delivery may be at least more than 10. In some examples, the upper limit of high throughput number may be $10^5$ or more. For example, in high throughput cell transfection, the number of cells transfected in accordance with one example is at least in a range from about 20 to 30. The high-throughput delivery typically employs delivery of exogenous molecules to multiple cells by irradiating the cells, per exposure. One or more of robotic, data processor, controller, detectors, and related software may be used to achieve high throughput delivery.

A method of delivering exogenous molecules comprises, providing a plurality of cells, wherein each of the cells has a cell membrane, and adding a plurality of exogenous molecules to the cells. The method further comprises, exposing the cells to an IR optical beam to permeabilize the cell membrane of the cells, and delivering the exogenous molecules to the cells through the permeabilized cell membrane, wherein an average power density of the IR light at the optical focus is in an order of at least greater than or equal to $10^4$ W/cm$^2$.

As noted, at least one of the methods uses lower average power density of the IR light at the optical focus, such as in an order of $10^4$ W/cm$^2$, unlike other methods presently used for optical based delivery that have a much higher average power density, as revealed in literature. In one or more examples, the average power density of light used, at the optical focus is in an order of about $10^4$ W/cm$^2$ to $10^5$ W/cm$^2$. The use of reduced average power density results in increased cell viability even after prolonged exposure. In these examples, the peak power density is in a range of about $10^8$ W/cm$^2$ to $10^9$ W/cm$^2$. The average power density is a ratio of absolute power and the illumination area. The peak power density may be calculated from average power density by multiplying it by a ratio T/t, where T is a period of pulse repetition (20 ns in this example) and t is a duration of each laser pulse (100 fs).

In one or more examples of the method, the IR optical beam is relatively defocused compared to the focused beam used for other optical based delivery methods. The optical beam is incident on an area, which is larger than an area covered by a single cell. Therefore, the defocused IR optical beam irradiates multiple cells present on an area of irradiation. In some examples, the area of irradiation of the IR optical beam is about 50 to 200 μm$^2$. In one examples, the area of irradiation of the IR optical beam is about 100 to 200 μm$^2$. The cells are placed on the area of irradiation for IR exposure to permeabilize the cell-membrane. The number of cells that are irradiated depends on the density of the cells at the time of exposure and on the area of exposure. If the density of the cells is high, the number of cells exposed to IR is more compared to the number of cells exposed in case of lower density.

The method employs a defocused IR optical beam with an average optical power of at least greater than 50 mW. In some examples, the method uses a light source with an average optical power of about 100 to 500 mW. One example of the method employs an average optical power of the light source, which is in a range from about 100 to 200 mW. A defocused low power IR light may be incident multiple times over a population of cells. This method enables higher efficiency for delivery of exogenous molecules with minimal cell death.

The method may be configured to permeate cells and deliver exogenous molecules into the cells by varying focus of the IR optical beam. Various optical elements are used to change the focus of the optical beam, such as variable-focus liquid crystal lens, spatial modulator and wave front modulator to move optical focus rapidly. In some examples of the method, using different optical lenses, the focus of the optical beam may be changed. In one example, a variable-focus liquid crystal lens may be used to change the focus of the optical beam. The focus of the optical beam may be changed depending on the requirement of the application, such as delivery of exogenous molecules or cell ablation. The IR generates heat on a focused area of irradiation and may cause cell death or cell ablation.

A pulse optical beam may be used to suppress the heat generation on the cell membrane, which may consequently minimize the cell damage. In some examples of the method, the IR optical beam that is used for delivery of exogenous molecules is a pulsed light source such as laser or laser diode. In one example, the IR optical beam that is used for delivery of exogenous molecules is a laser beam. The method employs IR light source that generates a laser beam after passing through one or more of the variable-focus liquid crystal lens, spatial modulator or wave front modulator and by moving optical focus rapidly. By reducing the intensity of the laser beam, optimizing pulse duration of the beam, minimizing the average power of the beam, or using a broader area of irradiation, the viability of the cells may be increased. For example, the area of irradiation of this method is a broader area of about −50 to 200 μm$^2$, wherein the produced heat may be diffused on the multiple cells, and that reduces the damage of the irradiated cells.

The laser beam has a good directionality, and may be focused or defocused depending on its requirement using an optical microscope. These properties enable the laser beam to increase permeability of the cell membrane by irradiating the cells. Various types of laser may include, but are not limited to, the YAG laser, the eximer laser, the Ar ion laser, the nitrogen laser, or the nitrogen-excited color laser. One or more examples of the method operate in the longer wavelengths, and the light source may be fiber-based, which enables compact implementation of the delivery method. In one example of the method, the erbium-doped fiber laser is used to produce a defocussed laser beam for irradiating the cells. In one example, the method employs erbium-doped fiber laser at an wavelength of 1.55 μm, unlike other expensive and large solid-state lasers, e.g., Nd:YAG or Ti:Sapphire laser.

The focusing depth of the laser on the cell membrane may be controlled using appropriate optical elements. In one example, the processing accuracy for optical based delivery may also be controlled by optimizing the irradiation energy and the number of irradiations on the cells. The conditions for irradiation of the cells using laser may be changed depending on the requirement of the optical delivery, or the type of the cells where the exogenous molecules are delivered.

Typically, temporal focusing of light is used for positioning the shortest pulse at a desired location along the beam propagation path. Temporal focusing is achieved by illuminating a diffraction grating at particular angle (called Bragg angle, and equal to 30 degrees in this example) and collecting diffracted light at the sample by a focusing lens. The method of temporal focusing relies on creating a uniform gradient of temperature, which increases efficiency of transfection. In some examples, the laser is temporally focused for wide field illumination to irradiate the cells. Wide field illumination occurs when the optical energy is spread among large number of cells, in contrast to localized illumination when only a few cells are illuminated. The high efficiency of laser-based optical delivery may be achieved using repeated sublethal laser pulses without affecting cell-viability.

In some examples, the cells are thereby irradiated with multiple laser pulses with lower intensity of laser beam. Efficiency of laser based delivery increased significantly with increasing number of laser pulses. In one example, the laser pulse has a wavelength greater than at least 700 nm. In some examples, the width of each of the laser pulses is less than about 200 fsec. In another example, the pulse width of the laser used for the method is about 100 fsec. The varied number of laser pulses is incident upon the cell membrane with a repetition rate of at least greater than 1 MHz in one example, and the repetition rate of the pulses is at least greater than 10 MHz in another example. In some examples, the repetition rate of the pulses is at least greater than 50 MHz. In one or more examples, the laser pulses are repeated for a variable number of times with an interval of about 2 to 20 ns between each of the pulses. In one example of the method, laser pulses are repeated for a variable number of times with an interval of about 10 ns. In one example, the laser has a wavelength greater than 700 nm, pulse width greater than 1 psec, and repetition rate greater than 1 MHz.

The time of exposure to a laser beam may be controlled, so that the exposure may be enough for making the cell membrane permeable, and at the same time the exposure may not be reached a threshold for killing the cells. For effective optical-based delivery, a beam residence time for irradiation is one of the significant factors. In some examples of the methods, the exposure of the cells for about 1 to 10 seconds is enough for permeabilizing the cell membrane. In one example, the cells are exposed to a laser beam for about 5 to 20 seconds. The beam residence time for irradiation of a defocused laser beam is about 1 to 30 seconds, which is sufficient for high throughput optical based delivery. The exposure of cells may be even higher, may be for few minutes, for example 1 to 5 minutes, wherein the cell viability is maintained. In one example, the beam residence time is about 10 minutes, and the cells are viable after this prolonged exposure, as the intensity of the light is optimized to a lower value.

The method of optical delivery typically employs a defocused laser beam and irradiates the cells, resulting in a temporary permeabilization of the cell membrane. The permeabilization may results by producing sub-micrometer holes on the membrane to facilitate uptake of exogenous materials into the cells. The permeabilization may be the results of absorption of multi-photon and cascade ionization of water molecules on the cell membranes.

For efficient delivery of exogenous molecules into the cells, a thermal gradient may be generated across the cell membrane of each of the cells, which may permeabilise the cell membrane temporarily. The thermal gradient may be the results of excitation of the water molecules present in the liquid media comprising the cells. Unlike other optical delivery that uses visible and NIR light (300 nm~1064 nm), the method employs an IR light source with longer wavelengths (1~10 μm), which have higher water absorption. The higher water absorption results in a larger thermal gradient in the sample in the IR than in the visible. The IR light encompasses the near infrared (700 nm to 1.4 μm), shortwave infrared (1.4 μm to 3 μm), mid-infrared (3 μm to 8 μm) and portions of the long infrared (8 μm to 10 μm). In one example, water molecules absorb light at a wavelength of about 1.55 μm to generate light induced microscopic thermal gradient across the cell membrane. The lipid molecules present on the membrane also plays a significant role to induce the thermal gradient.

In some examples, a large difference of absorption coefficients between the water of the liquid media comprising the cells and the lipid of the cell membrane plays an important role. The difference of absorption coefficients between the water and the lipid results generation of a thermal gradient across the cell membrane. In one aspect, a large thermal gradient facilitates the cell membrane poration process. In another aspect, the exogenous molecules may move from a high temperature environment to a low temperature environment.

The optical spectra used for the delivery of exogenous molecules according to one aspect of the method, having a wavelength of about 1.55 μm. As shown in table 1, conventional optical based delivery methods generally use optical spectra with wavelength of about 0.532 μm, wherein the absorption coefficient of water is 0.000447 cm$^{-1}$ and that of lipid is 0.01002 cm$^{-1}$ and the ratio of water:lipid is about 0.045. Some of the conventional methods use optical spectra with a wavelength of about 0.80 μm, wherein the absorption coefficient of water is 0.02 cm$^{-1}$ and that of lipid is 0.004 cm$^{-1}$ and the ratio of water:lipid is about 5. In some examples of the methods, the optical spectra is used for delivery of exogenous molecules at a wavelength of 1.55 μm, wherein the absorption coefficient of water is 10.5 cm$^{-1}$ and that of lipid is 0.08 cm$^{-1}$ and the ratio of water:lipid is about 131.25. The optical based delivery at the wavelength of 1.55 μm provides more than at least an order of magnitude higher difference of absorption coefficients between water and lipid, and the ratio of ~131.25, which is almost about 2900 times higher than the ratio for delivery at 0.532 μm and 26 times higher than the ratio for delivery at 0.80 μm. As can be seen in Table 1, the required power density at the optical focus is strongly dependent on the wavelength of the light source and the absorption coefficient of the sample at said wavelength. Specifically, higher absorption coefficients require lower power densities at the sample to achieve the same level of optical delivery. For example, moving further into the IR beyond 1.55 μm, absorption coefficient of water is higher in orders of magnitude. This allows the power density at the optical focus to be adjusted accordingly.

TABLE 1

Ratio of absorption coefficients of water and lipid at different wavelengths.

| | | Wavelength (μm) | | |
|---|---|---|---|---|
| | | 0.532 | 0.80 | 1.55 |
| Absorption coefficient (l/cm) | Water | 0.000447 | 0.02 | 10.5 |
| | Lipid | 0.01002 | 0.004 | 0.08 |
| | Water/lipid | 0.045 | 5 | 131.25 |

In one or more examples, the optical based delivery method is transfection. Genetic materials may be delivered to the cells using the laser exposure. Use of pulse laser is even more beneficial, as the pulse laser with lower intensity does not affect the cell morphology or cellular-function. As noted in this example, the use of defocused laser on a broader area enables transfection of more than one cell at a time.

In one example, the method allows molecular delivery of multiple cells simultaneously, such as transfection of multiple cells. The illumination pattern of the near IR optical beam enables multiple cells to uptake exogenous molecules. In one or more examples, the number of cells transfected by this method is at least in a range from about 20 to 30. In one example, the method allows a high throughput transfection of multiple cells. The high-throughput delivery typically employs delivery of exogenous molecules to multiple cells by irradiating the cells, per exposure. For achieving an automated high throughput delivery, use of one or more of robotic, data processor, controller, detectors, and related software may be desirable. In one example of the method, by changing illumination pattern of the near IR light, optical delivery of exogenous molecules to single cell may also be possible.

As noted in the optical based delivery, the exogenous molecules are transferred from outside to the cells, wherein the cells are selected from bacterial cells, yeast cells, plant cells or animal cells. The efficiency of optical based delivery is not dependent on cell types, unlike other chemical transfection methods. In case of plant cells, the cell wall may be removed using any conventional method. The spheroplast forms after removing the cell-wall, and may be used for cell transfection using optical based delivery. The cells may be placed in a static or moving condition. In one example, the cells may be placed on a holder, wherein the cells are in static condition. In another example, the cells may be moved through a channel while illuminating by laser for optical based delivery of exogenous molecules.

As noted in the optical based delivery, at least one of the methods is employed to deliver exogenous molecules into the cells, wherein the exogenous molecules comprise small molecules, genetic materials, proteins, peptides, organelle, physiologically active materials, and targeting agents. The genetic material comprises deoxyribonucleic acids (DNA), ribonucleic acids (RNA), small interfering ribonucleic acids (siRNAs), micro RNA, nucleic acid analogues, oligonucleotides, plasmids, and chromosomes.

In some examples, the genetic material is DNA. The DNA may be a double-stranded DNA (dsDNA), single-stranded DNA (ssDNA), plasmid DNA, synthetic DNA, organelle DNA or circular DNA. In one example, the DNA has a recombination site. In some examples, the exogenous molecules are DNA, wherein the DNA has a target sequence. The target sequence may code for an expression product. In some examples, the target sequence may code for an expression product, which is capable of eliciting an immune response in an organism. In one or more examples, the target sequence may be derived from at least one of: a bacterium, virus, fungus, parasitic organism and non-parasitic organism. In some examples, the target sequence codes for a surface antigen of the bacterium, virus, fungus, parasitic organism or non-parasitic organism from which the target sequence is derived. An illustrative use of optical based delivery is to express recombinant proteins, such as the proteins which are able to generate a signal (e.g. expression of a green fluorescent protein) and that is useful in tracking cells (e.g. during cell therapy). The exogenous molecules may be used to elicit an immune response in an organism.

In one or more examples, the exogenous molecule is short interfering RNA or siRNA. RNA interference (RNAi) is a natural antiviral defense mechanism for silencing gene expression and presently is a powerful technology to knockdown genes in mammalian cells for functional analysis or gene-therapy. siRNA is useful for inhibiting the expression of a gene of interest, such as a gene with a defect results a phenotypic, a genotypic or both effect. Typically, siRNA is intracellular double stranded RNA that regulates post transcriptional gene silencing pathways. Using siRNA techniques, specific gene function may be determined through targeted gene knockdown. An antiviral response may be overcome by using delivery of siRNA as exogenous molecules. The optical based delivery may directly be introduced siRNA into the cytoplasm through the temporarily permeable membrane, without forming endosome. Therefore, the delivery of siRNA using the optical based method may bypass the endosomal processing pathways. In one example, the genetic material may be micro RNA.

In one example, the exogenous molecules are coupled to one or more agents. The agents may be selected from a group consisting of a bead, an affinity tag, a signal peptide, a nanoparticle, a vesicle, a lipid and combinations thereof. A bead or affinity tag may be coupled to the exogenous molecules. For example, when glutathione-S-transferase (GST) tag sequence is coupled to DNA, the recombinant DNA enables isolation and purification of a protein encoded by the same DNA using respective affinity column. For another example, a signal peptide may be coupled to a genetic molecule, such as a nuclear localization signal or NLS is coupled to DNA, wherein the recombinant DNA enters into a specific location of the cell, such as nucleus, using the NLS signal sequence.

One of the optical based delivery methods utilizes engineered nanoparticles that produce shock waves or localized heat upon light illumination. Targeted transfection may be performed by attaching engineered nanoparticles to the target cells. For example, metallic nanoparticles may be engineered for attaching the nanoparticle to the membrane of the target cells, and to generate high thermal gradient upon light absorption. In one example, carbon nanoparticles such as carbon nanotubes, carbon black, or graphene generates significant sound waves upon light absorption, which facilitates molecular uptake by the cells. In another example of the method, engineered nanoparticles may be suspended in the liquid media where the cells are placed, and the nanoparticles are used to generate significant sound waves that may help uptake exogenous molecules into the cells.

In one or more examples, the method of optical based delivery methods may also combine with other delivery methods. Such as, the laser exposure may be associated with treating the cells with one or more chemicals to increase the permeability of the cells. The method may comprise pre-treatment, simultaneous treatment or post-treatment of the cells. For example, magneto-transfection or magnetoporation may be used before the laser exposure. In this example, the magnetic force may align the cells, exogenous molecules, or combination of both at the optical focus, wherein the exogenous molecules are subsequently be delivered to the cells using the laser exposure. In some other examples, the permeability of the cell membrane may increase using various chemicals having mild effect on the cell membrane, and then the exogenous molecules are subsequently be delivered to the cells using laser beam. For example, use of calcium phosphate, cationic polymer such as polyethylene imine, or liposomes enables the cell membrane to uptake exogenous molecules, and the cells which are processed with such agents may easily be transfected with much higher efficiency.

Cell ablation is required in some of the applications, such as, to prevent stem cell differentiation, or to resist unlimited cell growth in different cellular pathways, such as apoptosis. Uncontrolled cell growth is a feature of malignancy, which may also be resisted using malignant cell ablation using laser treatment. The laser has an excellent light-condensing ability, and contributes no thermal influence upon a portion other than the area of irradiation of the laser beam. Depending on the vertical adjustment of the laser focusing, the intensity of the laser may be changed. The cells, which are required to be ablated, are generally placed at the focus of the laser beam. In case of optical based delivery, the cells are typically placed at the region which is out of focus for the laser beam. In one or more examples, the intensity of the laser may increase to an extent which is enough for ablating the cells. The beam residence time may also vary depending on the requirement of the application. In one example, the laser beam residence time or exposure time is optimized in combination with appropriate average power density of the laser, which may be sufficient to ablate or kill the cells. Similar efficiency may be achieved either by increasing the beam residence time while the power density of the laser is low, or by keeping the beam residence time small, while the power density of the laser is high. In some examples, the beam residence time and the power density of the laser may need to be adjusted at the same time for optimizing the optical based delivery process.

Optical based delivery of the exogenous molecules into the cells has efficiencies comparable with the methods commonly used. Small molecules, such as PI, calcein, dextran, phalloidin, and macromolecules, such as DNA, RNA and siRNA are successfully delivered to the cells using laser exposure, in accordance with one embodiment of the invention.

Figure 2:
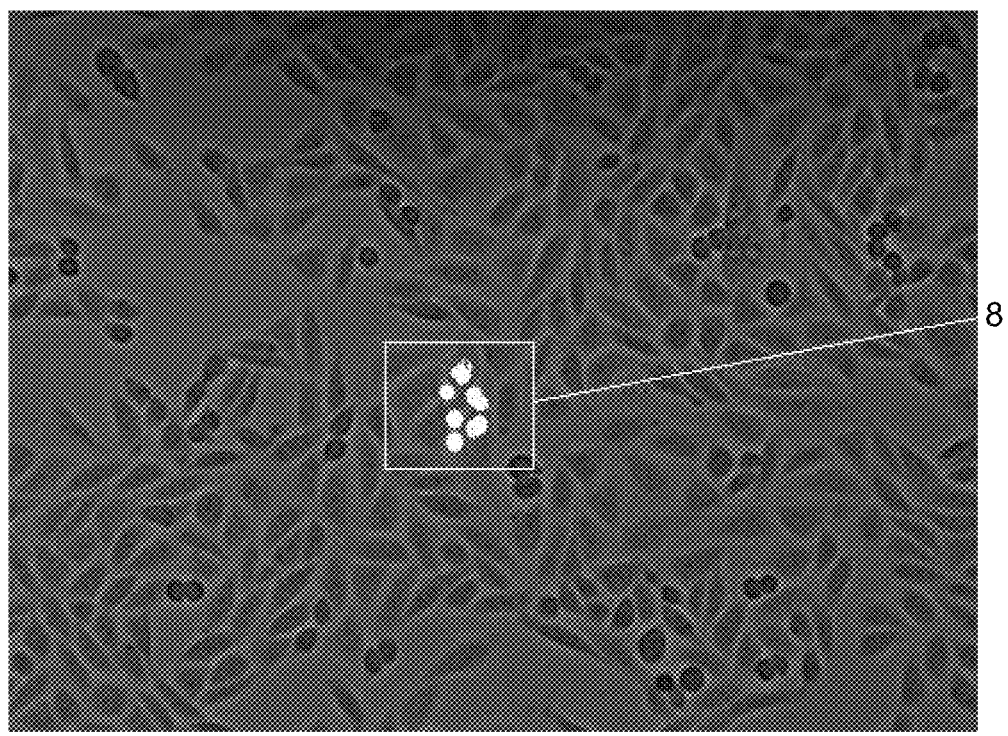
FIG. 2 is a fluorescence microscopic image of CHO cells expressing PI after IR exposure using temporal focusing according to an embodiment of the invention.
Figure 3A:
FIG. 3 is a series of fluorescence microscopic images illustrating phalloidin uptake of (A) CHO cells and (B) NIH 3T3 cells using IR exposure according to an embodiment of the invention.

For example, PI is a small molecular (6.68 kDa) fluorescent dye, which is generally impermeant to membrane of the live cells, and therefore the dye is unable to introduce into the live (or viable) cells. However, after laser exposure using one example of the method, the CHO viable cells 2 are able to uptake PI, as shown in FIG. 1A. The uptake of PI is prominent compared to the negative control (FIG. 1C), wherein the viable cells 6 are not exposed to laser. As the dead cells easily uptake PI, the dead CHO cells 4 expressed PI are served as a positive control (FIG. 1B). In one example, CHO cells 8 uptake PI using temporal focusing of laser beam (FIG. 2), wherein the laser has a power density of 45 mW and the cells are exposed for 15 mins. In some examples, phalloidin is introduced into the CHO cells 10 (FIG. 3A). In some other examples, dextran is also introduced into the CHO cells. Therefore, delivery of various types of molecules is possible using laser based optical delivery.

Figure 3B:
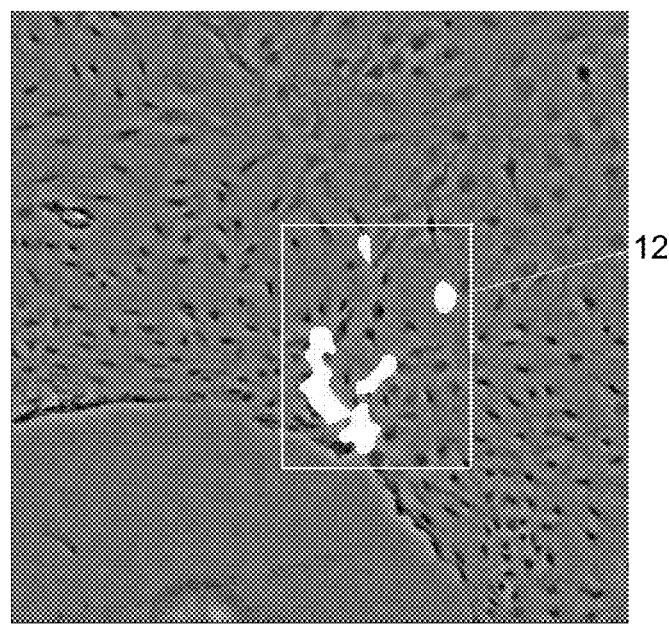

The optical based delivery is cell type independent. Various types of cells are subjected to exogenous molecular delivery using laser exposure in accordance with one example of the method. In one example, phalloidin is introduced into the CHO cells 10 as well as into NIH 3T3 cells 12, as shown in FIG. 3A and FIG. 3B respectively.

Figure 4A:
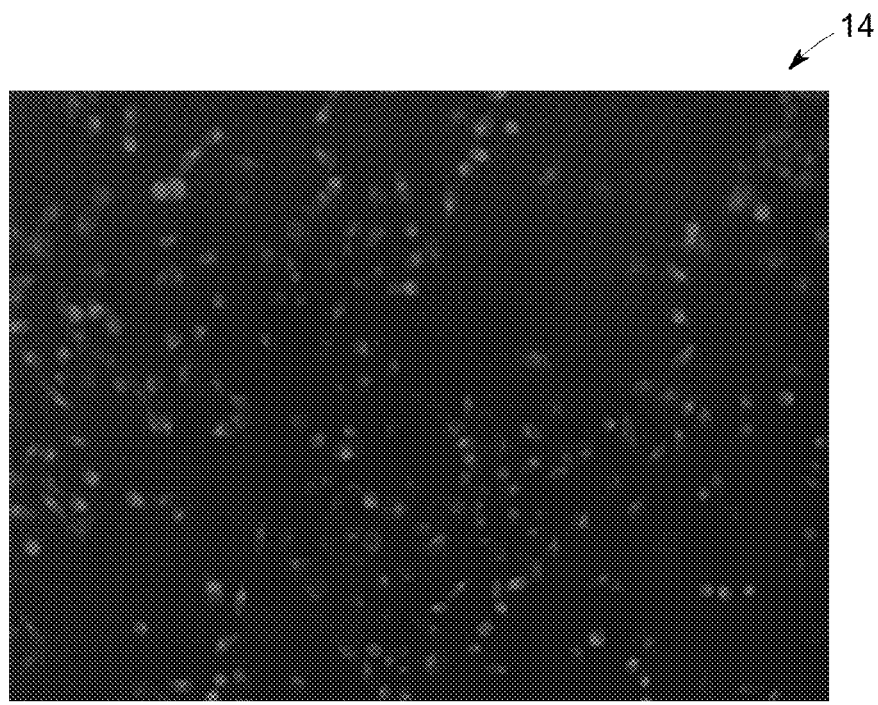
FIG. 4 is a series of fluorescence microscopic images of CHO cells illustrating expression of (A) PI and (B) calcein using IR exposure according to an embodiment of the invention.
Figure 4B:
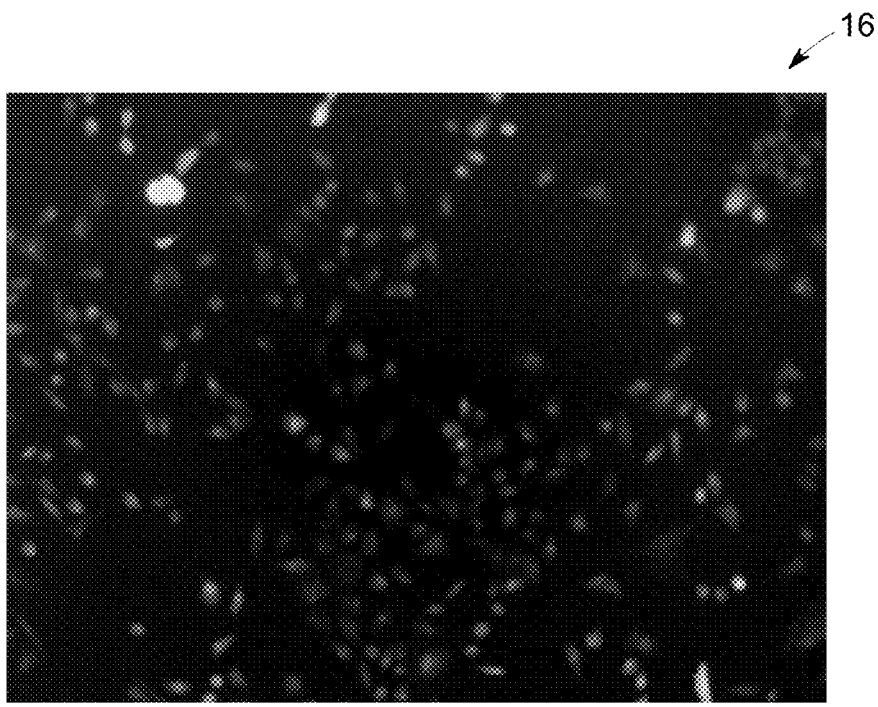

PI is generally known to identify dead cells in a population of cells, whereas calcein is another small molecular dye that is used to identify the viable cells. The non-fluorescent calcein enters into the viable cells and converts to green-fluorescent calcein on hydrolysis of acetoxymethyl ester by intracellular esterases. Therefore, use of calcein may provide a solution to verify the viability of the CHO cells that uptake PI after laser exposure. Using same dose of laser for the same exposure time, CHO cells those are already expressed PI showed red fluorescent color 14 (FIG. 4A), are also able to uptake calcein, as shown by green fluorescent color 16 (FIG. 4B). Therefore, the CHO cells are viable cells and the cell-membrane of the CHO cells become permeable to PI after laser exposure in accordance with one example of the method.

Figure 5A:
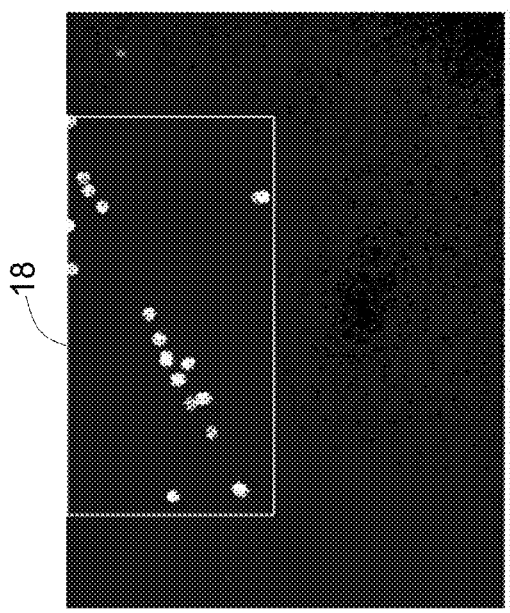
FIG. 5 is a series of images for CHO cells transfected with FITC tagged siRNA on laser exposure according to one embodiment of the invention using fluorescence microscopic image (A) and a bright field microscopic image merged with fluorescence image (B); compared to a negative control without laser exposure (C), and a positive control using lipofectamine (D).
Figure 5B:
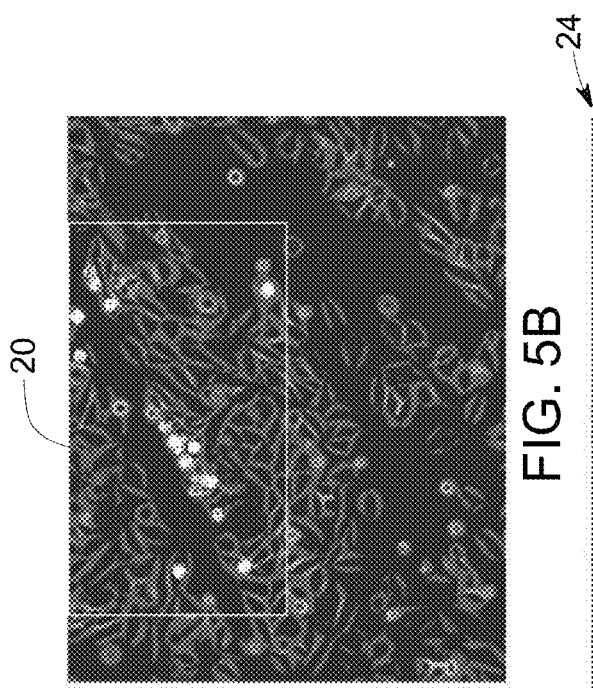
Figure 5C:
Figure 5D:
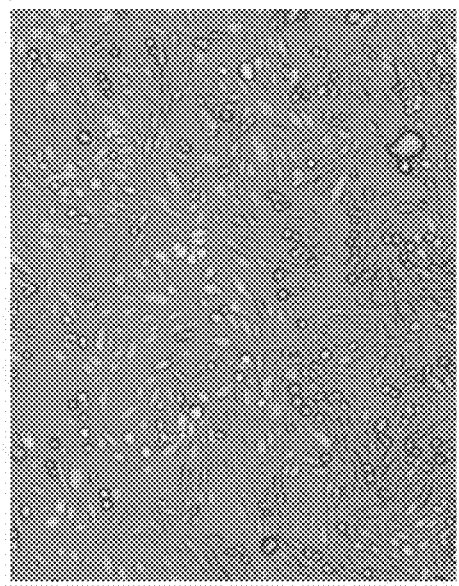

Transfection of siRNA to the CHO cells is illustrated in an example of the method, as shown in FIGS. 5A and 5B. In one example, CHO cells are exposed to laser in presence of FITC tagged siRNA (siRNA-FITC) as test sample. FIG. 5A shows the siRNA-FITC transfection into the cells as bright green spots 18. FIG. 5B shows the same cells of FIG. 5A after merging with bright field microscope 20. The sample contains siRNA-FITC with CHO cells, without using any laser exposure, serves as a negative control 22. On over-night incubation of a sample contains Lipofectamine™ 2000 and siRNA-FITC serves as a positive control 24. FIGS. 5C and 5D are images of negative control without exposing to laser beam (no green spots) 22, and positive control using Lipofectamine™ 2000 where the bright green spots 24 reflect transfection of siRNA, respectively.

FIG. 6 shows vertical adjustment of laser focusing on cells for cell ablation, wherein a sample holder 26 holds the cell sample, and a lens is used to focus 28 on the sample holder when the defocused region is 30. In one example, as the cells are placed in focus 28, the power density of the laser is more on the holder comprising cells 26. Therefore, the cells are exposed to a laser with an average power density above at least a threshold value of $10^5$ W/cm$^2$, which is enough to ablate the cells on exposure. In another example, the cell holder 26 remains in the same physical position, by vertical adjustment 32 of the temporal focusing, the lens shifts the focus 28 of the optical beam, for example to an upward position or a downward position, so that the defocused region 30 of the optical beam is positioned on the sample holder comprising cells 26. Therefore, the power density of the optical beam at the defocused region is less, which helps to transfect multiple cells at a time.

Figure 7A:
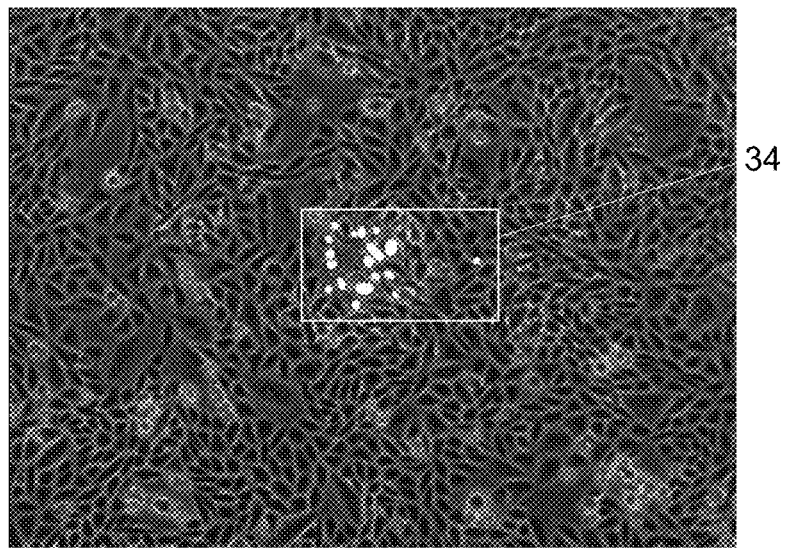
FIG. 7 is a bright field microscopic image merged with fluorescence microscopic image of (A) CHO cells expressing PI after laser exposure according to one embodiment of the invention, and (B) laser ablated CHO cells after laser exposure according to another embodiment of the invention.
Figure 7B:
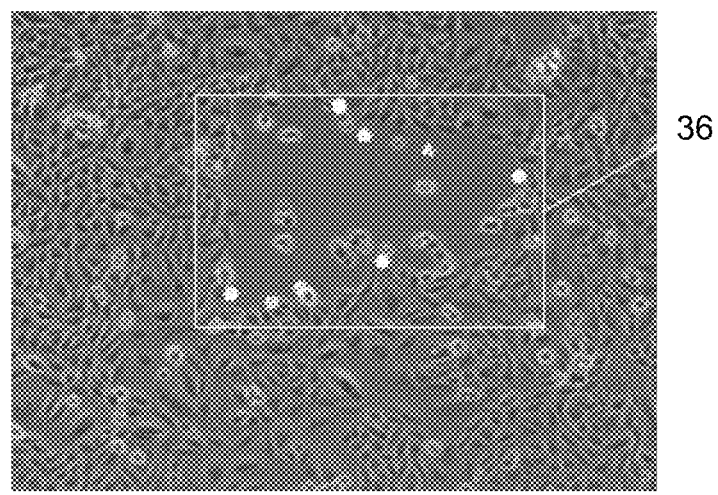

FIG. 7A shows PI uptake of CHO cells 34, using a defocused beam. In similar condition, by changing vertical adjustment of the laser focusing, CHO cells are ablated 36 using a focused beam, as shown in FIG. 7B. In this example, the ablation occurred at the average power density of $0.54 \times 10^5$ W/cm$^2$; the time of exposure was 5 min, with the laser pulse has a wavelength greater than at least 700 nm and width of each of the laser pulses is less than about 200 fsec.

The following examples are intended to be illustrative of suitable methods for delivery of various exogenous molecules into the cells. Such methods are not the only methods suitable for use in the various aspects and embodiments of the invention and should not be viewed as limiting the scope of the invention.

EXAMPLES

Materials: The Chinese Hamster Ovary (CHO) cells (cat#CCL-61), B35 rat neuroblastoma cells (cat#CRL-2754) and NIH 3T3 cells (cat #CRL-1658) were purchased from ATCC®, Manssas, Va., USA. Rat mesenchymal stem cells (cat#R492K-05) were purchased from Cell Applications Inc., San Diego, Calif., USA. Propidium Iodide or PI (cat#P4864-10ML) was purchased from Sigma, St. Louise, Mo., USA. Phalloidin Alexa Fluor 568 (cat#A12380) was purchased from Invitrogen, USA. Trypan blue was purchased from Invitrogen (cat#T10282). Cell-count was performed using Countess® Automated Cell Counter, Invitrogen, USA. Calcein AM fluorescent dye was purchased from BD Biosciences (cat #354216). Dextran fluorescein 3000 was purchased from Invitrogen, (cat#D-3305). Lipofectamine™ 2000 was purchased from Invitrogen™ cat#11668-019. FITC tagged siRNA was purchased from Invitrogen (catalog no. 2013). 4% PFA and 0.1% Triton X-100 were purchased from Sigma. DMEM supplemented with 10% FBS was purchased from ATCC®. F12K media supplemented with 10% FBS was purchased from ATCC®.

Cells and medium: CHO cells (ATCC® cat#CCL-61) were cultured in F12K media supplemented with 10% FBS according to the manufacture ATCC® protocol. Rat mesenchymal stem cells (cat#R492K-05) were cultured using Rat Marrow Stromal Cell Growth Medium Kit according to the Cell Applications Inc. protocol. B35 rat neuroblastoma cells (cat#CRL-2754) and NIH 3T3 cells (cat #CRL-1658) were cultured in DMEM supplemented with 10% FBS according to the ATCC® protocol.

Example 1

Optical Delivery of Molecules in Different Cells

CHO cells (cat#CCL-61) were cultured in F12K media supplemented with 10% FBS according to the manufacture protocol. Cells were used at an early passage, between passage 4 and passage 10. Experiments were carried in 35 mm dishes or 24 well plates. CHO cells were seeded at 0.7-1×10^5 cells/well for the 24 well plate and 3-4×10^5 cells/dish for the 35 mm dishes. Cell-count was measured using Countess® Automated Cell Counter (Invitrogen) according to the manufacture protocol. Cells were grown to 65~75% confluence. 10 μl of confluent cell suspension was mixed with 10 μl Trypan Blue stain 0.4% (from Invitrogen) and the mixture was fed into the cell counter.

The cells were examined after 24 h of seeding for their morphology and viability. Fresh media was added to the cells in a final volume of 1 ml for cells seeded in 24 well plate and 2 ml for the cells seeded in 35 mm dish. Cells were incubated with PI at the standard concentration of 1 μg/ml for 5 min prior to laser exposure. A negative control was generated where cells were incubated with PI, without laser exposure. A positive control was generated wherein, the cells were fixed and then permeabilized with 4% PFA and 0.1% Triton X-100, and then incubated with PI at the standard concentration of 1 μg/ml for 5 min before laser exposure.

Figure 1:
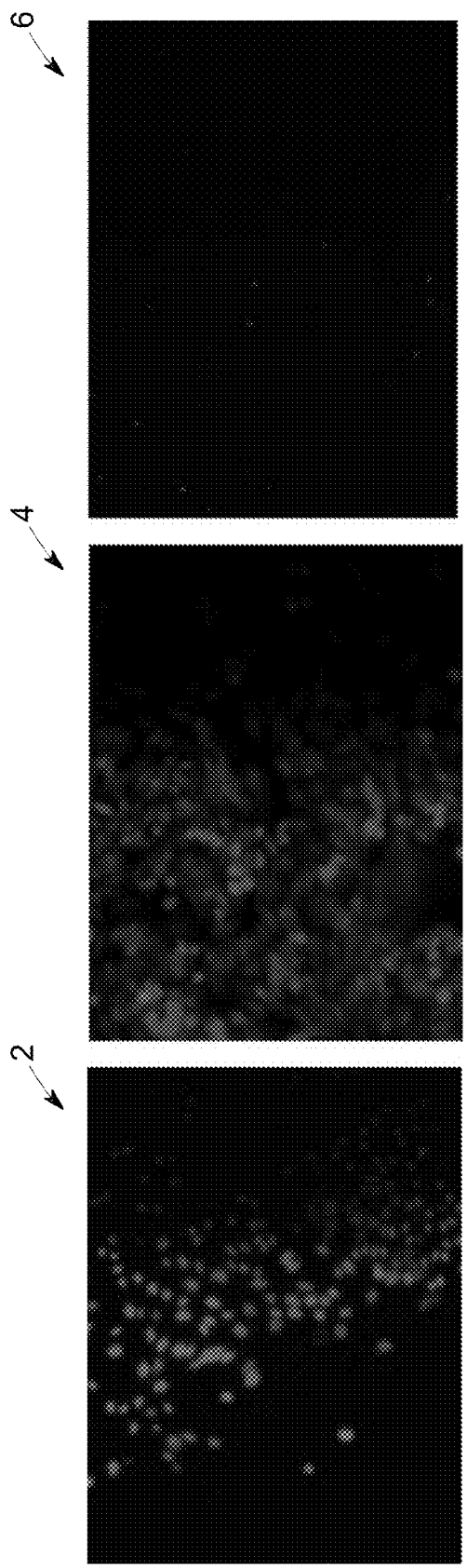
FIG. 1 is a series of fluorescence microscopic images of (A) Chinese Hamster Ovary (CHO) cells expressing propidium iodide (PI) after IR exposure according to an embodiment of the invention, (B) dead CHO cells expressed PI after fixation with PI (positive control), and (C) CHO cells incubated with PI without IR exposure (negative control).

A femtosecond laser (center wavelength=1.55 μm, pulse width ~100 fsec, repetition rate ~50 MHz) irradiation was performed on the petridish with a beam spot diameter of ~100 μm. The peak power density of a laser used was $250 \times 10^6$ W/cm$^2$, and the exposure duration was about 5 min. FIG. 1 shows the cell images taken after 1 hour of the exposure, wherein the exposure was for 5 mins. FIG. 1A shows PI expressed by CHO cells 2 with respect to the positive control as shown in FIG. 1B. In positive control, the dead CHO cells 4 were fixed with PI, and the cells expressed PI uptake. Dead cells typically uptake PI and that shows in FIG. 1B. The negative control is shown in FIG. 1C, wherein the CHO cells 6 and PI were mixed, and incubated without laser exposure.

Optical based delivery using temporal focusing: FIG. 2 shows the image of the cells taken after 1 hour of the exposure, wherein the exposure was for 5 min. FIG. 2 shows PI expressed by CHO cells, wherein the PI is introduced into the cells using temporal focusing. The laser was passed through diffraction grating with a 30° Bragg angle, and collected at the cell holder by a 10× objective lens with numerical aperture 0.25. Cells were exposed for 15 min to a laser with average power density of 20 kW/cm$^2$. Such illumination provided uniform gradient of temperature.

The optical delivery may also be assayed using various different cell types and different exogenous molecules. Various molecules were tested for optical delivery, such as, calcein, dextran, and phalloidin. Different cell types, such as CHO cells, rat mesenchymal stem cells, B35 rat neuroblastoma cells and NIH 3T3 cells uptake phalloidin molecules. As noted, 24 h post seeding, the cells were examined for their morphology and viability. Fresh media was added to the cells and the cells were incubated with 200 nM Phalloidin-Alexa Fluor 568. Several controls were generated such as a negative control, where cells were incubated with Phalloidin-Alexa Fluor 568 without laser exposure, and a positive control, where cells were fixed and permeabilized by PFA 4%/Triton X-100 0.1% and incubated with Phalloidin-Alexa Fluor 568 followed by laser exposure. Different cell types, such as CHO cells 10 (FIG. 3A) and NIH 3T3 cells 12 (FIG. 3B) show uptake of phalloidin molecules. Therefore, optical based molecular delivery is cell type independent.

As CHO cells show uptake of PI, calcein (Example 2), phalloidin, dextran and siRNA (Example 3) molecules, it established that the optical based delivery is useful for various types of molecular delivery.

Example 2

Viability Assay for Cells after Laser Exposure

To demonstrate cell viability of the exposed cells, a calcein assay was performed. The most cells expressed PI as PI was introduced into the cells through light illumination. The cells which uptake PI were further subjected to laser exposure after incubation with calcein. Cells were exposed to laser for 10 mins in presence of PI. 24 h post laser exposure, cells were washed with Hank's Balanced Salt Solution (HBSS) and 10 ul calcein was added in 1 ml of HBSS at a final concentration of 5 μM. Cells were incubated with calcein for 1 h at 37° C. After 1 h, cells were washed one time with HBSS and imaged by Nikon Eclipse TE2000U inverted research microscope. After imaging the cells, HBSS buffer was washed and cells were incubated in fresh HBSS media. They were again imaged at 48 h and 72 h post-delivery. The laser beam used for delivery had average power density $25 \times 10^4$ W/cm$^2$, pulse width of about 100 fsec. FIG. 4A shows fluorescence microscopic image of CHO cells with PI uptake, about 48 hours after the laser exposure. The cells which already uptake PI are also expressed calcein as shown in FIG. 4B. It proves that the cells expressed PI were live cells, as calcein can only be taken by live cells.

Example 3

Transfection of siRNA

CHO cells were seeded at $4 \times 10^5$ cells per 35 mm dish using 2 ml media. The cells were seeded one day prior to the laser exposure. On the next day, 20 siRNA-FITC from a stock solution of 10 pmole/μl was added to each of the cell sample in 2 ml F12K media, 10 min prior to the laser exposure. Cells were exposed to laser for about 10 min/50 μm diameter of the illuminated area and visualize the cells right after the laser exposure and 24 h post laser exposure. FIG. 5A shows the FITC tagged siRNA transfection into the cells using defocused laser having power density of $0.4\times10^4$ W/cm$^2$. FIG. 5B shows the same cells with bright field microscope after merging with fluorescence image. Incubating 20 siRNA-FITC (from a stock solution of 10 pmole/μl) with CHO cells, without using any laser exposure, served as a negative control as shows in FIG. 5C.

A positive control for siRNA transfection was performed using Lipofectamine™ 2000. siRNA and Lipofectamine 2000 complex was formed before adding to cells. 10 pmol siRNA-FITC and 2 μl Lipofectamine™ 2000 were mixed and incubated for 20 min at room temperature to form (siRNA-FITC)-Lipofectamine™ 2000 complex for 24-well format. Depending on the nature of the target gene, transfecting cells at higher densities may also be considered when optimizing the various conditions. Add the (siRNA-FITC)-Lipofectamine™ 2000 complexes to each well containing cells in a F12K media. The mixture of cells and (siRNA-FITC)-Lipofectamine™ 2000 complex mixed gently by rocking the plate back and forth. The cells were incubated at 37° C. in a $CO_2$ incubator for 24-96 hrs. The complete media (contain F12K and 10% FBS) may be changed after 4-6 hours, and washed to remove excess Lipofectamine™ 2000. The siRNA-FITC was transfected to the cells which is reflected as bright green spots as shown in FIG. 5D and served as a positive control.

Example 4

Cell Ablation Using Laser Exposure

In this example, the cells were ablated using a laser having intensity of $0.54\times10^5$ W/cm$^2$ or higher; the time of exposure was 5 min, with the laser pulse has a wavelength greater than at least 700 nm and width of each of the laser pulses is less than about 200 fsec. The focusing lens had focal length of 30 mm. The CHO cells were transfected (FIG. 7A), wherein the cells were placed out of focus of the laser beam. In similar condition, by changing vertical adjustment of the laser focusing, CHO cells are ablated. The average power density of laser was at least 10 times higher for cell ablation compared to the average power density of laser beam used for cell transfection assay. The CHO cells were ablated using the same laser beam while focusing on the cells (FIG. 7B).

The scope of the invention is defined by the claims, and may comprise other examples not specifically described that would occur to those skilled in the art. Such other examples are intended to be within the scope of the claims.

What is claimed is:

1. A method of delivering exogenous molecules, comprising:
    providing a plurality of cells having a cell membrane;
    adding a plurality of exogenous molecules to the cells;
    exposing the cells to an infra-red (IR) light to permeabilize the cell membrane for delivering the exogenous molecules to the cells through the permeablized cell membrane,
    wherein an average power density of the IR light at the optical focus is greater than or equal to an order of $10^4$ W/cm$^2$, and a peak power density is greater than or equal to an order of $10^8$ W/cm$^2$, and
    wherein an area of irradiation of the IR light is in a range from about 50 to 200 μm$^2$.
2. The method of claim 1, wherein an average power of the IR light is in a range from about 100 to 200 mW.
3. The method of claim 1, wherein the IR light is a laser.
4. The method of claim 3, wherein the laser is a pulse laser with a wavelength greater than 700 nm, a pulse width greater than 1 psec, and a repetition rate greater than 1 MHz.
5. The method of claim 1, wherein the cells are exposed for about 1 second to 10 minutes.
6. The method of claim 1 is a transfection.
7. The method of claim 6, wherein the transfection is a high throughput transfection.
8. The method of claim 1, wherein the cells are selected from a group consisting of bacterial cells, yeast cells, plant cells, and animal cells.
9. The method of claim 1, wherein the cells are in a static or a moving condition.
10. The method of claim 1, wherein the exogenous molecules are selected from the group consisting of small molecules, genetic materials, proteins, peptides organelle, physiologically active material, and targeting agents.
11. The method of claim 10, wherein the genetic material comprises deoxyribonucleic acids (DNA), ribonucleic acids (RNA), siRNAs, micro RNA, nucleic acid analogues, oligonucleotides, plasmids, and chromosomes.
12. The method of claim 11, wherein the genetic material is DNA.
13. The method of claim 12, wherein the DNA has a recombination site.
14. The method of claim 12, wherein the DNA comprises a target sequence that codes for an expression product.
15. The method of claim 14, wherein the expression product is capable of eliciting an immune response.
16. The method of claim 11, wherein the genetic material comprises siRNA.
17. The method of claim 1, wherein the exogenous molecules are coupled to one or more agents selected from a group consisting of a bead, an affinity tag, a signal peptide, a nanoparticle, a vesicle, a lipid and combinations thereof.
18. The method of claim 1 further comprising, adding one or more nanoparticles.
19. The method of claim 1, wherein exposing the cells to the IR light is followed by use of magnetic field to co-localize the cells and exogenous molecules at the optical focus.
20. The method of claim 1, wherein exposing the cells to the IR light is associated with treating the cells with one or more chemicals to increase permeability of the cells.
21. The method of claim 1, further comprising exposing some of the cells to the IR light by keeping the cells at the optical focus for ablating the cells.

* * * * *